United States Patent [19]
Willis et al.

[11] Patent Number: 5,853,709
[45] Date of Patent: Dec. 29, 1998

[54] SHAVING COMPOSITION AND METHOD FOR PREVENTING PSEUDOFOLLICULITIS BARBAE

[75] Inventors: Isaac Willis, Atlanta, Ga.; Adu Gyamfi Darkwa, Olympia Fields; Apolonio L. Villanueva, Northbrook, both of Ill.

[73] Assignee: Johnson Products Co., Inc., Chicago, Ill.

[21] Appl. No.: 766,395

[22] Filed: Dec. 12, 1996

[51] Int. Cl.$^6$ ...................................................... A61K 7/15
[52] U.S. Cl. ............................ 424/73; 424/405; 424/406; 424/606; 424/650
[58] Field of Search .............................. 424/73, 405, 406, 424/606, 650

[56] References Cited

U.S. PATENT DOCUMENTS

| | | | |
|---|---|---|---|
| 4,944,939 | 7/1990 | Moore | 424/73 |
| 5,567,428 | 10/1996 | Hughes | 424/401 |
| 5,652,274 | 7/1997 | Martin | 514/724 |
| 5,653,970 | 8/1997 | Vermeer | 424/70.24 |

*Primary Examiner*—Neil S. Levy
*Attorney, Agent, or Firm*—Kirschstein, et al.

[57] ABSTRACT

A topically applied shaving composition for use by a human subject suffering from or prone to development of pseudofolliculitis barbae is disclosed. The composition comprises as its active ingredient about 0.01–5% by weight of a bacteriostatic/hemostyptic agent, and an aqueous or water-miscible solvent, a volatile silicone and a thickening agent. A method of removing hair from a hairy skin area of such a subject comprising the application of a topical shaving composition containing about 0.01–5% by weight of a bacteriostatic/hemostyptic agent prior to removal of the hair by shaving, tweezing or waxing, is also disclosed.

52 Claims, 3 Drawing Sheets

SHAVING COMPOSITION AND METHOD FOR PREVENTING PSEUDOFOLLICULITIS BARBAE

BACKGROUND OF THE INVENTION

1. Field of the Invention

This invention relates to shaving cream compositions and methods for allowing the shaving of hair-bearing areas of the human body without causing or aggravating the skin disease pseudofolliculitis barbae.

2. Description of the Prior Art

Pseudofolliculitis barbae (PFB) is a chronic inflammatory condition of the hair-bearing areas of the lower face and neck as well as other hairy skin areas (such as the nuchal, bikini and leg areas) and is characterized by the following: irritating "bumps", soreness, itchiness, and dark or red discolored spots of the affected skin areas. The condition is a direct result of shaving, occurring in more than 80% of African Americans and about 22% of other racial groups. It may lead to infection, permanent dark discoloration, scarring, and even keloid formation in some individuals. PFB is also commonly referred to as "razor burns" and "ingrown hairs".

Studies of PFB have revealed that it results in most instances from an inflammatory response incited by hairs which are "ingrown" or trapped underneath the cornified layer (stratum corneum) of the skin, or hairs which emerge from their follicles with a sharp curl and whose points penetrate back into the skin to form a "pseudo follicle" (thus, "pseudofolliculitis"). The hair trapped beneath the skin or the ends which have repenetrated the skin from the surface cause the eruption of swollen pus-filled lesions known as perifollicular papules which blanket the shaved skin area. This reaction is commonly called "bumping up". PFB can be caused not only by shaving but also by waxing and tweezing the hairy area.

Various methods have been practiced in the art for treating and/or preventing PFB. These include abstention from shaving; the application or administration of topical corticosteroids, topical or systemic antibiotics, tretinoin cream or gel, topical anti-inflammatory agents and astringents; attempted hair epilation and use of chemical depilatories; mechanical extraction of hairs from the bumps; and use of scrub brushes or similar devices, None of these solutions have been particularly viable, acceptable to patients or effective.

In May 1991 a paper was presented by Joseph P. Pavlichko at the Annual Scientific Seminar of the Society of Cosmetic Chemists proposing the use of the polymeric quaternary ammonium salt of hydroxyethyl cellulose known as Polyquaternium-10 at about 2% concentration in a shaving gel formulation intended to prevent the development of PFB. This gel product purportedly caused varying degrees of improvement in the skin condition of 7 of 10 volunteers who used the gel over a three-month period. Nevertheless, the use of Polyquaternium-10 in shaving gel or cream formulations has not been widely acknowledged or developed as a viable solution for the problem of PFB, which is particularly common and severe among black males.

SUMMARY OF THE INVENTION

It is an object of the invention to provide shaving compositions, and methods of preventing or treating PFB employing said compositions, which are safe, effective and easy to use. It is a further object of the invention to provide such compositions and methods which are superior to any which were disclosed in the prior art and which may be used by males and females prone to or suffering from PFB.

In keeping with these objects, and others which will become apparent hereinafter, the invention resides, briefly stated, in a shaving lotion or cream composition for use by human subjects suffering from or prone to development of PFB comprising a bacteriostatic/hemostyptic agent, a solvent, a volatile silicone and a thickener. The composition may also contain a nonionic or cationic polymeric conditioning agent and a surfactant, as well as fragrances, cooling agents, coloring agents, topical anesthetics, preservatives and other conventional ingredients used in topical cosmetic or toiletry formulations.

The method of the invention for treating or preventing PFB in humans comprises the application of a shaving composition comprising a bacteriostatic/hemostyptic agent to a hairy skin area, particularly a skin area prone to or already exhibiting the symptoms of PFB, prior to the shaving, waxing or tweezing of that skin area. The composition may be applied alone before hair removal or as a pre-treatment followed by application of a conventional shaving cream or gel.

DETAILED DESCRIPTION OF THE INVENTION

The novel shaving composition of the invention may take any physical form known in the art for compositions applied to hair-bearing areas of the skin prior to removal of hair from those areas by shaving, waxing, tweezing or other means of hair removal. Such physical forms include creams, lotions, gels, liquids, and the like. However, the preferred embodiments of the novel composition are a shaving lotion or shaving cream.

The lotion or cream composition of the invention comprises as its active ingredient a bacteriostatic/hemostyptic compound, preferably selected from the group consisting of stannous fluoride, stannous chloride, salicylic acid, alpha hydroxy acids and sodium monofluorophosphate. The active ingredient is preferably dissolved or dispersed in a stabilizing vehicle, for example, glycerin or propylene glycol, and is present in the shaving composition in a weight concentration range of about 0.01–5%, and preferably about 0.1–2%, based on the weight of the total composition.

The bacteriostatic/hemostyptic agent or agents included in the shaving compositions of the invention play an important role in the prevention/treatment of PFB. These agents inhibit bacterial growth and swelling upon nicking or scratching of the skin during shaving. These actions help suppress the development or aggravation of razor bumps and assist the healing process.

The preferred bacteriostat for purposes of the invention is stannous fluoride which is currently used safely and effectively in tooth pastes and gels and in aqueous solutions for topical application.

The composition of the invention further comprises as pharmaceutically inert ingredients one or more aqueous or water-miscible solvents, volatile silicones and thickening agents.

The lotion or cream composition of the invention also comprises in its preferred embodiments one or more ingredients from each of the following categories: humectants; nonionic or cationic polymeric conditioning agents; surfactants; and topical anesthetic agents, and may also include as desired for particular formulations fragrances, cooling aid ingredients, coloring agents, emulsifiers and preservatives.

The solvents used in the composition of the invention may be water, an alcohol such as ethyl or isopropyl alcohol or a mild, water-miscible astringent such as witch hazel. The solvent components of the shaving composition may also comprise a mixture of one or more of the foregoing solvents, in proportions deemed appropriate by those skilled in the art of formulating cosmetic lotions and creams. The precise weight percentage of the solvent or solvent mixture in the cream or lotion composition and the proportion of various solvents used in the case of a solvent mixture will depend on various factors, including, by way of illustration, the desired thickness or viscosity of the finished composition, the identity and quantity of the ingredients to be dissolved in a given formulation of the composition and the sensitivity or disease (PFB) status of the skin to be treated. A milder and less irritating solvent system should be used for the most sensitive skin while a more astringent solvent can be employed for less sensitive or less affected skin areas.

The volatile silicones used in the composition of the invention are low-viscosity cyclomethicone fluids which are clear, essentially odorless and non-toxic, non-greasy and non-stinging. These cyclomethicone fluids generally comprise a mixture of dimethylcyclosiloxane trimers, tetramers and pentamers.

Examples of commercially available cyclomethicone fluids suitable for use in the compositions and methods of the present invention include OSI Fluids VS-7207, VS-7158 and VS-7349 (OSI Specialities, Inc.) and Dow Corning 244 and 344 Fluids (Dow Corning Corp., Midland, Mich.).

Thickening agents for use in the novel compositions include any thickening or viscosity-increasing agents which are appropriate for use in a topical cream or lotion cosmetic formulation, especially cationic polymers and copolymers, e.g., SALCARE SC-96 (Allied Colloids Inc.), a cationic copolymer of Polyquaternium 37 with propylene glycol dicaprylate dicaprate and PPG-1 Trideceth-6 ester. Alternative thickening agents include SALCARE SC-91, SC-92 and SC-95 (all from Allied Colloids).

The preferred humectant for use in the novel compositions is glycerin, but other humectants such as sorbitol, propylene glycol, hexylene glycol and hydrogenated starch hydrolysate may be used, as well as any other humectant compositions known in the art as suitable for use in topical shave lotions or creams. In the preferred embodiment, Superol Glycerin, USP is used as the humectant ingredient and also serves as the primary solvent or dispersing vehicle for the bacteriostatic, hemostyptic ingredient stannous fluoride.

Nonionic and cationic polymeric agents used in the invention are preferably acrylamide polymers or copolymers. These polymers serve as conditioning agents to soften beard and body hairs and prevent their re-entry or re-penetration into the skin, and also help to soften and condition the skin. Examples of commercially available conditioning agents suitable for use in the invention include SALCARE SC-60 (Allied Colloids Inc., Suffolk, Va.), which is copolymer of acrylamidopropyl-trimonium chloride and acrylamide copolymer and SALCARE SC-10 (Allied Colloids) or MERQUAT 550 (Calgon Corp., Pittsburgh, Pa.), both of which are aqueous solutions of Polyquaternium 7, a cationic copolymer of dimethyldiallyammonium chloride and acrylamide. Alternative polymeric conditioning agents include Polyquaternium 4, Polyquaternium 10, Polyquaternium 39, hydroxyethylcellulose and guar gum.

Sufactants useful in the novel lotion or cream compositions include, in particular, those which are self-solubilizing in aqueous systems and which also provide lubricity and impart a silky texture on skin and hair. A preferred surfactant is AVAMID 150 (Mona Industries, Paterson, N.J.), a mixture of avocadamine DEA and avocado oil. This surfactant also helps stabilize stannous fluoride in glycerin and maintains the activity level of that agent by raising the pH of the composition to a less acidic level. Other amide diethanolamine surfactants which may be used include lauramide DEA, soyamide DEA, cocamide DEA, and capramide DEA.

Preservatives for the novel composition may be any standard cosmetic preservative, particularly those such as methyl paraben and imidazolidinyl urea which in low concentrations do not irritate sensitive or PFB-diseased skin but which effectively inhibit bacterial and fungal growth in the composition.

The concentration ranges by weight of the above ingredients, based on the weight of the total lotion or cream composition, are shown below. In each case, the percentage ranges given are for the aggregate of all ingredients coming within the listed category (e.g., all solvents or all silicones).

|  | % of composition (w/w) | |
| --- | --- | --- |
| INGREDIENT | BROAD RANGE | PREFERRED RANGE |
| Bacteriostats (stannous fluoride, etc.) | 0.01–5 | 0.1–2 |
| Solvents | 50–90 | 70–90 |
| Volatile Silicones | 0.5–10 | 2–8 |
| Thickening Agents | 0.5–5 | 1–4 |
| Humectants | 0–15 | 2–10 |
| Conditioning Agents | 0–15 | 1–12 |
| Surfactants | 0–10 | 0.1–3 |
| Preservatives | 0–2.0 | 0.1–1.0 |

Optional ingredients which may be included in certain embodiments of the novel shaving compositions include fragrances of the type conventionally used in shaving creams and lotions intended for sensitive or allergic skin, coloring agents selected from FDA-approved cosmetic pigments and color additives, and preservatives and other additives intended to increase stability and shelf life. A further category of optional ingredients in the composition are topical anesthetic agents, particularly lidocaine and benzocaine. These agents not only reduce the pain and irritation experienced by PFB-sufferers both during and after shaving, they also possess some bacteriostatic and hemostatic properties.

The composition of the invention may also contain a cooling aid component comprising skin cooling agents (e.g., peppermint oil and menthol) and/or fragrance to provide a fresh sensation and scent on the skin which remains after shaving.

The ingredients of the shaving lotion or cream compositions may be mixed and formulated to produce the finished product by any means known to those skilled in the art of cosmetic and toiletry formulations. By way of illustration, water or other aqueous solvent or solvent system is added first to a manufacturing tank and then the nonionic or cationic polymeric agents, if any, are added with constant stirring so that they are dispersed well in the solvent, whereupon warming of the batch in the tank is begun to maximize gelation. Next the bacteriostatic agent (in its vehicle) and volatile silicone are added to the tank together with any humectant being utilized, and further mixing is performed until the batch is uniform and free of undissolved particles. After cooling, the thickening agent or agents are added, again under continuous mixing, until the batch becomes thick and uniform.

A surfactant may then added to the batch and mixed well, whereupon the batch turns creamier and whiter. Any cooling aids, fragrances, preservatives and the like may be added following the surfactant with further mixing until the batch is uniform and homogeneous.

The present invention also comprehends a method of treating or preventing PFB using the novel shaving lotion or cream compositions. The method comprises the application to a hairy skin area of a human subject suffering from or prone to the development of PFB, prior to shaving, waxing or tweezing the hairy area, of a thin coating of the novel composition. Application of the shaving lotion or cream of the invention may be followed directly by shaving, waxing or tweezing, or a further shaving composition, such as a standard shaving cream or gel, may be applied on top of the novel composition prior to initiating the hair removal process. In the latter case, the composition of the invention acts as a pre-shave treatment lotion or cream, but still serves to ameliorate any aggravation or eruption of PFB lesions.

The following Examples are illustrative of the novel compositions and methods of the invention as well as a test study performed to demonstrate the efficacy of the invention in enabling the shaving of hairy skin areas provoking or aggravating eruptions of PBS. These Examples are not intended, however, to limit the scope of the invention in any way or to set forth specific starting materials, manufacturing procedures or conditions or methods of using the novel compositions which must be employed exclusively in order to practice the present invention.

EXAMPLES 1–3

Shaving Lotion Compositions

Three different creamy white shaving lotion compositions were produced using the ingredients set forth below in Table 1, each ingredient being present in the compositions in the percentage by weight specified in the Table.

TABLE 1

| Ingredients | % of composition (w/w) | | |
|---|---|---|---|
| | Example 1 | Example 2 | Example 3 |
| Water | QS | QS | QS |
| SALCARE SC-60 (Allied Colloids) Acrylamidopropyltrimonium Chloride/acrylamide Copolymer | 1.00 | — | 1.00 |
| SALCARE SC-10 (Allied Colloids) Polyquaternium-7 (8.50%) | — | 12.00 | — |
| Glycerin, 99.5% | 5.00 | 5.00 | 5.00 |
| Stannous Fluoride, USP | 1.00 | 1.00 | 1.00 |
| OSI FLUID VS-7207 OR DOW CORNING 244 FL Cyclomethicone | 5.00 | 5.00 | 5.00 |
| SALCARE SC-96 (Allied Colloids) Polyquaternium 37/propylene Glycol Dicaprylate Dicaprate (and) PPG-1 Trideceth-6 | 2.50 | 2.50 | 2.50 |
| AVAMID 150 (Mona Industries) Avocadamide DEA (And) Avocado Oil | 0.50 | 0.50 | 0.60 |
| Cooling Aid | 0.10 | 0.10 | 0.10 |
| Methyl Paraben | — | — | 0.10 |
| Imidazolidinyl Urea | — | — | 0.15 |

The cooling aid component of each of the compositions of Examples 1–3 consisted of the following:

| Cooling Aid Ingredients | % (w/w) |
|---|---|
| Peppermint Oil (Triple Distilled) | 89 |
| Menthol Crystals, U.S.P. | 1 |
| FRESCOLAT ML (Haarmann & Reimer) (Menthyl Lactate) | 5 |
| FLORAL 85% BENZYL ALCOHOL (TFF Corp.) (Fragrance and Benzyl Alcohol) | 5 |

The manufacturing procedure used to produce each of the shaving lotion compositions was as follows:

In an appropriate size stainless steel manufacturing tank equipped with lightnin and variable sweep mixers, add water and form a vortex. Add Salcare SC-60 cationic conditioning agent and disperse it well. Start warming the batch to 60°–65° C. to maximize gelation. Add glycerin, stannous fluoride and cyclomethicone. Mix until batch is uniform and free of any undissolved particles. Cool to 30°–35° C. and add Salcare SC-96 thickener with both mixers on until the batch becomes thick and uniform.

Add the Avamid 150 surfactant and mix well. The batch will turn creamier and whiter. Add the cooling aid and mix for 15 minutes. Once batch is uniform and homogenous, stop all mixers.

All of the compositions produced were of a creamy lotion consistency and were non-oily, non-staining and had a pleasant fragrance and feel.

The specifications for the lotion product of Example 1 were as follows:

| Appearance | White creamy lotion |
|---|---|
| pH: | 3.80–4.50 |
| Viscosity | 55–75 scale reading (LVT, spindle #4, 12 RPM, 1 minute). |
| NVM @ 105° C. 2 hours | 9.00–9.20 |
| Total Reducing Substances: | 0.060–0.065 meq/g |

EXAMPLE 4

Clinical Study

An investigator-blinded, crossover clinical study was conducted to evaluate the potential of a composition of the invention incorporated into a standard shaving regimen to reduce the incidence of PFB and its associated irritant and unpleasant sensory effects. The protocol of the study was as follows:

Test Materials
  Test shaving lotion (composition of Example 1)
  Inactive vehicle (composition of Example 1 without stannous fluoride)
  Razors (PFB Razors)
  Gentle Facial Soap (Purpose@)

Study Population

Twenty-four (24) individuals with mild to moderate PFB were selected from qualified male and female volunteers recruited at the study site. The inclusion criteria for subjects were as follows:

a. Eighteen (18) healthy Afro-American males and six (6) females between the ages of 18 and 45 who were free from any systemic or skin disorder (other than PFB) which might affect the evaluation of the test sites and/or results.
  b. The subjects had pre-existing PFB consisting of at least 20 lesions (papules and/or pustules) bilaterally spread on the face and neck in males and the thigh/groin area in females, as determined by a dermatologist.
  c. The subjects had a history of PFB and were unable to shave more frequently than two (2) to three (3) times per week because of their PFB condition,
  d. The subjects were regular users of safety razors.
  e. The subjects had a normal medical history.
  f. The subjects signed informed consent forms to participate in the study.

The following exclusion criteria were applied:

a. Subjects having used any systemic or tropical corticosteroids, antibiotics, antihistamines or retinoids within two (2) weeks of the study initiation.
  b. Subjects having used any depilatories or other PFB treatment products within two (2) weeks of the study initiation.
  c. Subjects with known allergies to shaving and facial skin care products.
  d. Subjects under medical care or those who expected to be within two months after inception of the study.

Test Procedures:

Study investigators counted PFB lesions (follicular papules and pustules) on the bearded areas of the face and neck of males and on the thighs and groins in females. The lesion counts were made and recorded separately for the treated and untreated (inactive vehicle only) sides of the face and neck or thighs and groin at Week 0-(pre-treatment), Weeks 1 and 2 (during initial treatment phase) and at weeks 3, 4 and 5 after crossover to active formulation only. Only active lesions were counted, with all macular and other post-inflammatory lesions disregarded.

A physician globally evaluated treatment effectiveness in the subjects using the following ratings:

Excellent: Completely clear, no evidence of any active lesions with the exception of an occasional minor lesion.
  Good: Condition greatly improved, almost completely clear with few lesions remaining.
  Fair: Condition much better, lesions greatly reduced, but still troublesome.
  No Change: No change in condition.
  Worse: Disease worse.

Study Protocol

Prior to the study all subjects were examined by a dermatologist to determine eligibility. A medical history was completed and gross observations were made of the skin test areas, hands and nails. The participants also completed questionnaires regarding their normal cleanser and moisturizer usage. Photographs of both sides of each subject's test areas were taken at baseline and at weeks 1, 2, 3, 4 and 5. Two weeks before the study commenced, all subjects discontinued use of any PFB treatments and any cleansers, moisturizers, depilatories, and shaving products other than those supplied by the clinic. Subjects were also instructed not to use any new fragrances or skin care or cosmetic products on the test areas during the study period.

Each subject was provided with a gentle facial soap (Purpose®), a PFB razor (Gillette Sensor Excel®) and the test products (the composition of Example 1 and a second composition containing the same vehicle but no active ingredient). Prior to daily shaving each subject washed his face or her thigh and groin area with soap and rinsed with warm water, followed by gentle towel blotting to remove excess water. The active test product was then applied to the right side of the test area in half the subjects and to the left side in the remaining half, and left on for 3 ½ minutes. Both groups applied the inactive product to the other side of their test areas. Both sides of the test area were then shaved with the PFB razor. After the completion of shaving, the entire test area was rinsed and patted dry to remove excess water, but leaving the skin moist. Subjects with ordinary dry skin were allowed to use Cetaphil® moisturizing cream over the entire test area as necessary.

After three weeks of the above phase of the study, all subjects were switched to use of only the active lotion formulation on both sides, with the above procedures otherwise being followed.

Study Results

1. All test sites treated with the lotion formulation of Example 1 showed marked improvement over the inactive vehicle ("untreated") sites. Improvement (i.e., a decrease in the number of inflamed papules and pustules) was rapid and decisive, with impressive clearing in as little as two weeks and complete clearing within three weeks on both the face and neck of men and the shaved groin and thigh of females.
  2. The untreated sites showed relatively little clearing, although there was mild clearing by the end of week two. There was an initial slight worsening at the end of the first week of observation of these control sites.
  3. After untreated sites were converted to treatment with the active composition, there ensued a very rapid clearing that mimicked the original treatment response on the opposite side.
  4. Essentially all subjects were clear by the fourth week of the study since they were all using the active lotion formulation.
  5. All treated sites remained clear with no complaints from the subjects when checked four (4) weeks after the end of the study.

Figure 1:
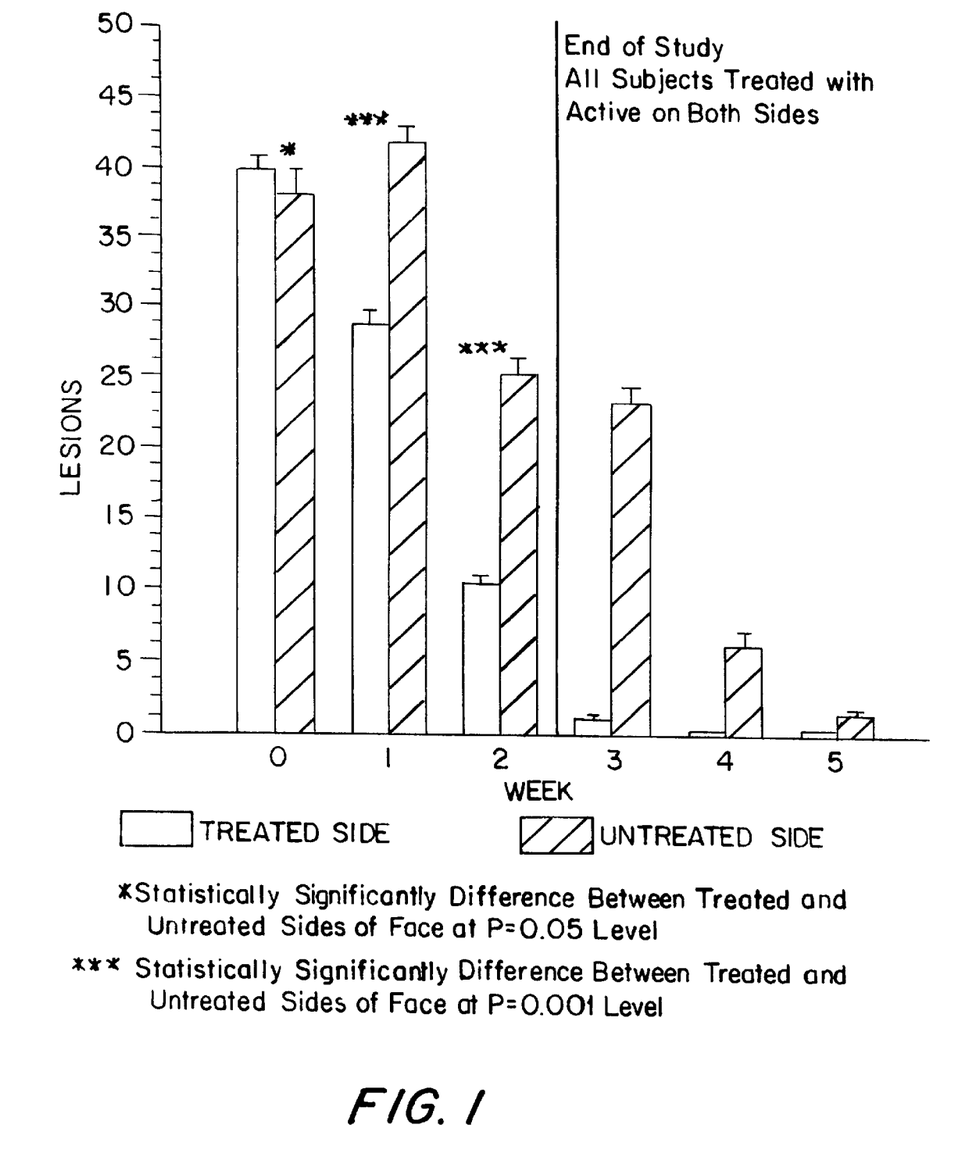
FIG. 1 is a bar graph reflecting the mean facial lesion count on the treated and untreated sides of the faces of eighteen (18) male human subjects who for two (2) weeks shaved one side of their faces using a lotion composition of the invention and the other side using the same composition vehicle but without the active ingredient, and then used the active lotion on both sides of their faces for three (3) weeks.
Figure 2:
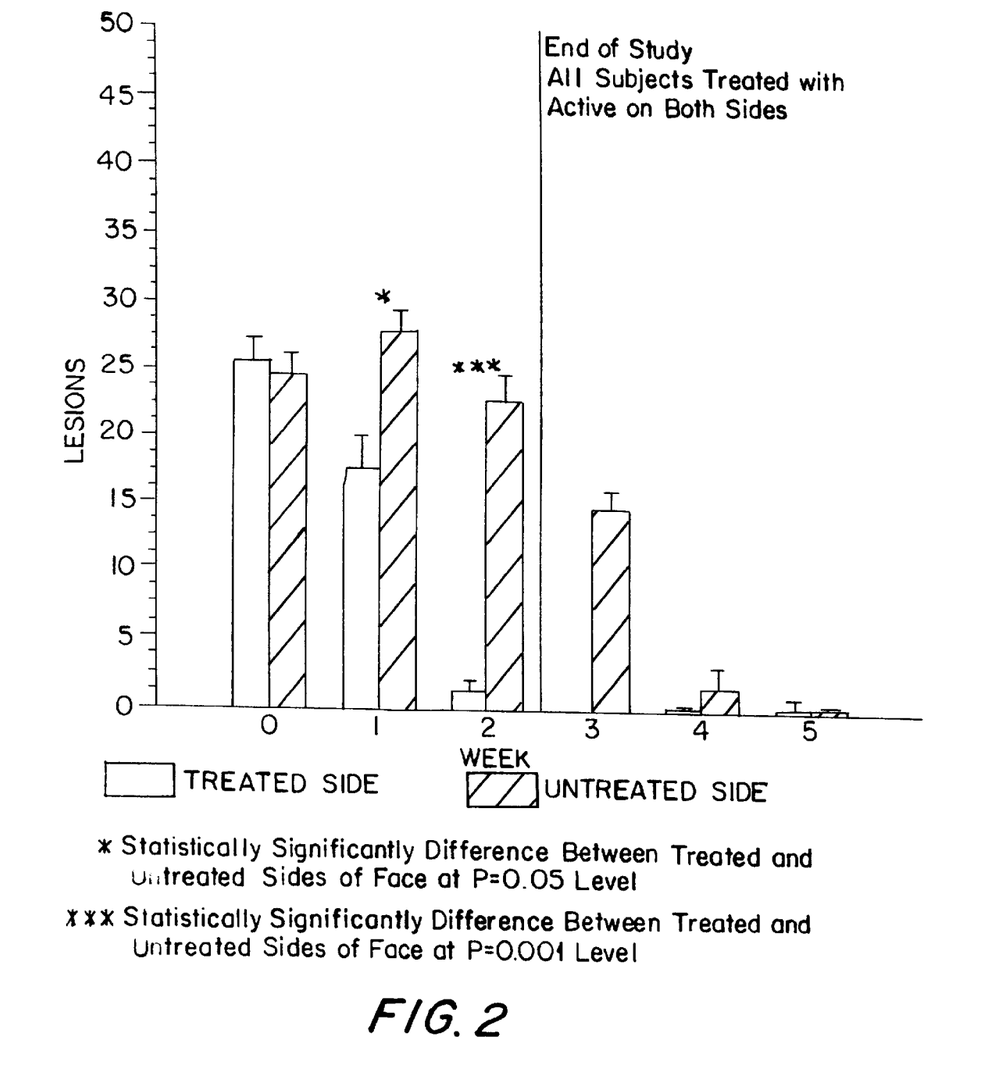
FIG. 2 is a bar graph reflecting the mean facial lesion count on the treated and untreated sides of the thigh/groin areas of six (6) female human subjects who for two (2) weeks shaved one side of their thigh/groin areas using a lotion composition of the invention and the other side using the same composition vehicle but without the active ingredient, and then used the active lotion on both sides of the test areas for three (3) weeks.

The results of the study in terms of mean lesion counts are illustrated in FIGS. 1 and 2. By the completion of one week of treatment, the mean lesion count on the treated sides of the subjects' faces was substantially lower than the lesion count on the untreated sides, and the difference was statistically significant at P=0.05 level (designated by the single asterisk). By week 2 the difference in lesion counts between the treated and untreated sides was statistically significant at P=0.001 level (designated by the triple asterisk). Although the study was terminated after three weeks, it appeared that continuation of treatment would have resulted in even lower lesion counts on the sides to which the test product had been applied.

EXAMPLE 5

Clinical Study

Another clinical study was conducted to evaluate the potential of a composition comprising only an active ingredient of the invention (stannous fluoride) in a stabilizing vehicle to reduce the incidence of PFB and its associated irritant and unpleasant sensory effects. The protocol of the study was as follows:

Test Materials

Test product (stannous fluoride 0.6% in a glycerin base)

Shaving Cream ( Edge Ultimate® for Sensitive Skin)

Razors (PFB Razors)

Gentle Facial Soap (Purpose®)

Study Population

Individuals with mild to moderate PFB were selected from qualified male volunteers recruited at the study site. The inclusion criteria for the volunteers were the following:

a. Twenty (20) healthy Afro-American male subjects between the ages of 18 and 45 who were free from any systemic or skin disorder (other than PFB) which might affect the evaluation of the test site and/or results.

b. The subjects had pre-existing PFB consisting of at least 20 lesions (papules and/or pustules) bilaterally spread on the face and neck as determined by a dermatologist.

c. The subjects had a history of PFB and were unable to shave more frequently than three (3) times per week because of their PFB condition.

d. The subjects were regular users of safety razors.

e. The subjects had a normal medical history.

f. The subjects signed informed consent forms to participate in the study.

The following exclusion criteria were applied:

a. Subjects having used any systemic or topical corticosteroids, antibiotics, antihistamines or retinoids within two (2) weeks of the study initiation.

b. Subjects having used any facial depilatories or other PFB treatment products within two (2) weeks of the study initiation.

c. Subjects with known allergies to shaving and facial skin care products.

d. Subjects under medical care or those who expected to be within two months after inception of the study.

Test Procedures

A study investigator counted PFB lesions (follicular papules and pustules) on the bearded areas of the face and neck. The lesion counts were made and recorded separately for the right and left sides of the face and neck at Week 0 (pre-treatment), Weeks 1, 2 and 3 (during treatment) and at post-treatment. Only active lesions were counted, with all macular and other post-inflammatory lesions disregarded.

A physician globally evaluated treatment effectiveness in the subjects using the following rating:

Excellent: Completely clear, no evidence of any active lesions with the exception of an occasional minor lesion.

Good: Condition greatly improved, almost completely clear with few lesions remaining.

Fair: Condition much better, lesions greatly reduced, but still troublesome.

No Change: No change in condition.

Worse: Disease worse.

Study Protocol

Prior to the study all subjects were examined by a dermatologist to determine eligibility. A medical history was completed and gross observations were made of the facial area, hands and nails. The participants also completed questionnaires regarding their normal facial cleanser and moisturizer usage. Photographs of each subject's face were taken pre-and post-treatment. Two weeks before the study commenced, all subjects discontinued use of any PFB treatments and any facial cleansers, moisturizers, depilatories, and shaving products other than those supplied by the clinic. Subjects were also instructed not to use any new fragrances or skin care or cosmetic products on the face during the study period.

Each subject was provided with a gentle facial soap (Purpose®), a PFB razor, a shaving gel/lather (Edge Ultimate® for Sensitive Skin) and the test product. Prior to daily shaving each subject washed his face with soap and rinsed with warm water, followed by gentle towel blotting to remove excess water. The test product was then applied to the right side of the face and neck in ten subjects and to the left side of the face and neck in the remaining ten subjects. In each case the product was applied for two minutes, rinsed off and then re-applied. The conventional shaving gel was then applied first on the side of the face without the test product and then on the treated side of the face, and the untreated side was shaved first followed immediately by shaving of the treated side. After the completion of shaving, the entire face was rinsed and patted dry to remove excess water, but leaving the skin moist. Subjects with ordinary dry skin were allowed to use Cetaphil® moisturizing cream over the entire face as necessary.

In this study the test product could not be used alone as a pre-shave composition, as in Example 4, because the glycerin base with stannous fluoride, in the absence of the other components of the novel composition (solvents, silicones and thickeners) did not possess the necessary physical characteristics to serve as a lubricating shave product.

Study Results

Figure 3:
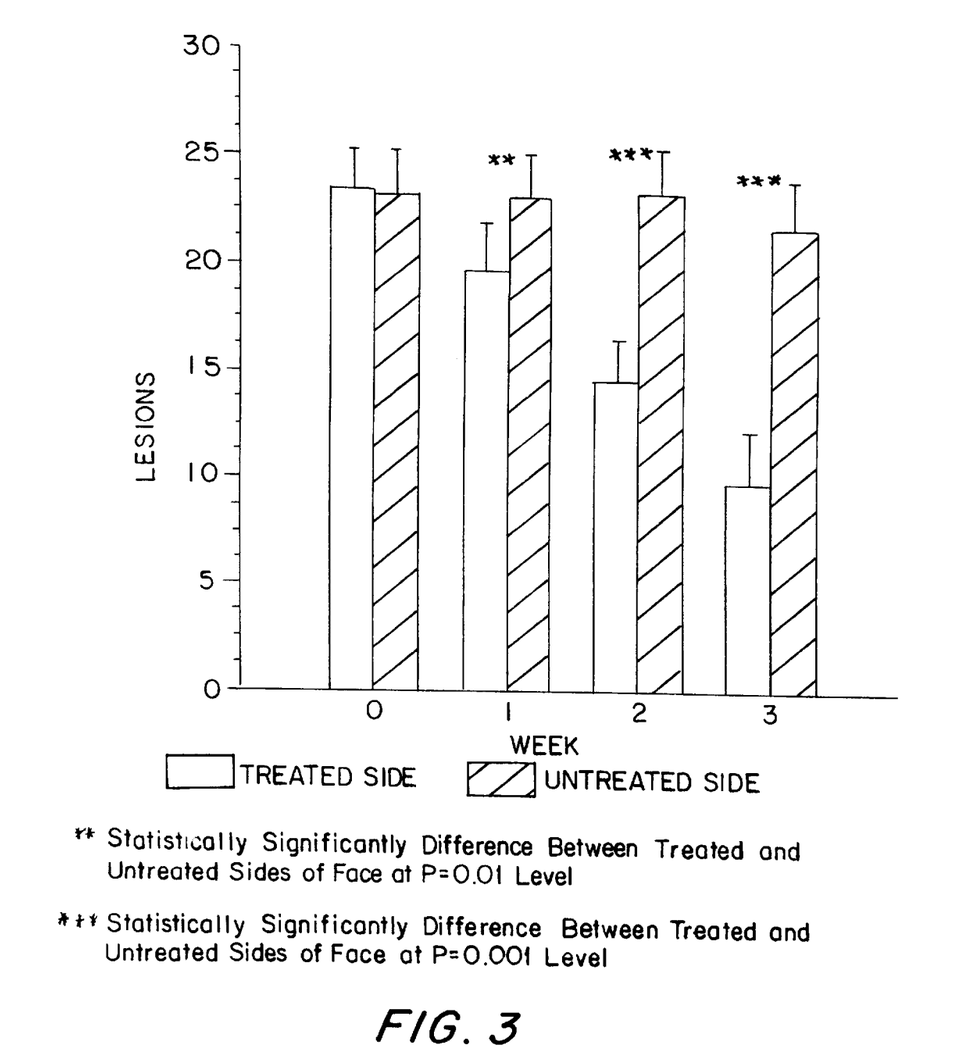
FIG. 3 is a bar graph reflecting the mean facial lesion count on the treated and untreated sides of the faces of twenty (20) human subjects who for three (3) weeks shaved one side of their faces using a standard shave gel alone and the other side with a bacteriostatic/hemostyptic agent (stannous fluoride) in a stabilizing glycerin base applied as a pre-treatment prior to application of the standard gel.

The results of the study in terms of mean lesion counts are illustrated in FIG. 3 By the completion of one week of treatment, the mean lesion count on the treated sides of the subjects' faces was substantially lower than the lesion count on the untreated sides, and the difference was statistically significant at P=0.01 level (designated on FIG. 3 by the double asterisk). By weeks 2 and 3, the difference in lesion counts between the treated and untreated sides was statistically significant at P=0.001 level (designated by the triple asterisk). Although the study was terminated after three weeks, it appeared that continuation of treatment would have resulted in even lower lesion counts on the sides to which the test product had been applied.

This study established that the stannous fluoride active ingredient was responsible for its anti-PFB activity. Hence, any cosmetically elegant composition with suitable characteristics for a shaving lotion, cream or gel (such compositions being well-recognized by those of ordinary skill in the art) which contains the requisite concentration of 0.1–5% by weight of stannous fluoride or of the other topical bacteriostatic/hemostyptic agents of the invention may be used in a method for preventing and/or treating PFB.

It has thus been shown that there are provided compositions and methods which achieve the various objects of the invention and which are well adapted to meet the conditions of practical use.

As various embodiments might be made of the above invention, and as various changes might be made in the embodiments set forth above, it is to be understood that all matters herein described are to be interpreted as merely illustrative.

What is claimed as new and desired to be protected by Letters Patent is set forth in the following claims:

We claim:

1. A topically applied shaving composition for use by a human subject suffering from or prone to development of pseudofolliculitis barbae or razor bumps, said composition consisting of about 0.01–5% by weight of a bacteriostatic/hemostyptic agent selected from the group consisting of stannous fluoride, stannous bromide, sodium monofluarophosphate and combinations thereof, and said composition further consisting of an aqueous or water-miscible solvent, about 0.5–10% by weight of a cyclomethicone and a thickening agent.

2. A composition according to claim 1 which is in the form of a lotion or cream.

3. A composition according to claim 1 which contains about 0.01–2% by weight of the bacteriostatic/hemostyptic agent.

4. A composition according to claim 1 wherein the bacteriostatic/hemostyptic agent is stannous fluoride.

5. A composition according to claim 4 which contains about 1% stannous fluoride.

6. A composition according to claim 1 which contains stannous fluoride dispersed or dissolved in glycerin.

7. A composition according to claim 1 which contains about 50–90% by weight of said aqueous or water-miscible solvent which is selected from the group consisting of water, ethyl alcohol, isopropyl alcohol, witch hazel and mixtures thereof.

8. A composition according to claim 7 which contains about 70–90% of said solvent.

9. A composition according to claim 7 wherein the solvent contains water.

10. A composition according to claim 1 which contains about 2–8% of the volatile silicone.

11. A composition according to claim 1 which contains about 0.5–5% by weight of the thickening agent.

12. A composition according to claim 11 which contains about 1–4% of the thickening agent.

13. A composition according to claim 1 wherein the thickening agent is a viscosity-increasing cationic polymer or copolymer.

14. A composition according to claim 13 wherein the thickening agent is a cationic copolymer of a quaternary compound and acrylamide.

15. A method of removing hair from a hairy skin area of a human subject suffering from or prone to development of pseudofolliculitis barbae, comprising:

a) applying to the hairy area a coating of a topical shaving composition containing as its active ingredient about 0.01–5% by weight of a bacteriostatic/hemostyptic agent selected from the group consisting of stannous fluoride, stannous bromide, sodium monofluorophosphate and combinations thereof, and said composition further containing an aquaeous or water-miscible solvent, a volatile silicone and a thickening agent; and b) removing the hair by shaving, tweezing or waxing the hairy area.

16. A method according to claim 15 wherein said composition is in the form of a lotion or cream.

17. A method according to claim 15 wherein said composition contains about 0.01–2% by weight of the bacteriostatic/hemostyptic agent.

18. A method according to claim 15 wherein the bacteriostatic/hemostyptic agent is stannous fluoride.

19. A method according to claim 15 wherein the bacteriostatic/hemostyptic agent is dissolved or dispersed in a stabilizing vehicle selected from the group consisting of glycerin or propylene glycol.

20. A method according to claim 19 wherein said composition contains stannous fluoride dispersed or dissolved in glycerin.

21. A method according to claim 15 wherein said composition contains about 50–90% by weight of said aqueous or water-miscible solvent which is selected from the group consisting of water, ethyl alcohol, isopropyl alcohol, witch hazel and mixtures thereof.

22. A method according to claim 21 wherein said composition contains about 70–90% of said solvent.

23. A method according to claim 15 wherein said composition contains about 0.5–10% by weight of the volatile silicone.

24. A method according to claim 23 wherein said composition contains about 2–8% of the volatile silicone.

25. A method according to claim 15 wherein the volatile silicone is a cyclomethicone.

26. A method according to claim 15 wherein said composition contains about 0.5–5% by weight of the thickening agent.

27. A method according to claim 26 wherein said composition contains about 1–4% of the thickening agent.

28. A method according to claim 15 wherein the thickening agent is a viscosity-increasing cationic polymer or copolymer.

29. A method according to clam 28 wherein the thickening agent is a cationic copolymer of a quaternary compound and acrylamide.

30. A method according to claim 15 wherein said composition further contains a humectant selected from the group consisting of glycerin, sorbitol, propylene glycol, hexylene glycol and hydrogenated starch hydrolysate.

31. A method according to claim 30 wherein said composition contains about 2–10% of said humectant.

32. A method according to claim 15 wherein said composition further contains about 0–15% by weight of a nonionic or cationic polymeric conditioning agent.

33. A method according to claim 32 wherein said composition contains about 1–12% by weight of said conditioning agent.

34. A method according to claim 32 wherein the conditioning agent is an acrylamide polymer or copolymer, hydroxyethylcellulose or guar gum.

35. A method according to claim 15 wherein said composition further contains about 0–10% by weight of a surfactant.

36. A method according to claim 35 wherein said composition contains about 0.1–3% of the surfactant.

37. A method according to claim 35 wherein the surfactant contains an amide diethanolamine.

38. A method according to claim 15 wherein said composition further contains a cooling aid component including peppermint oil or menthol.

39. A method according to claim 15 wherein said composition further contains a topical anesthetic agent selected from the group consisting of lidocaine and benzocaine.

40. A method according to claim 15 wherein said hairy area is an area of the face, neck, thigh or groin or is the bikini area of the subject.

41. A topically applied shaving composition for use by a human subject suffering from or prone to development of pseudofolliculitis barbae or razor bumps, said composition consisting of about 0.01–5% by weight of a bacteriostatic/hemostyptic agent selected from the group consisting of stannous fluoride, stannous bromide, sodium monofluarophosphate and combinations thereof, and said composition further consisting of an aqueous or water-miscible solvent, about 0.5–10% by weight of a cyclomethicone, a thickening agent, a humectant, about 0–15% by weight of a nonionic or cationic polymeric conditioning agent and about 0–10% by weight of a surfactant.

42. A composition according to claim 41 wherein said humectant is selected from the group consisting of glycerin, sorbitol, propylene glycol, hexylene glycol and hydrogenated starch hydrolysate.

43. A composition according to claim 42 which comprises about 2–10% of said humectant.

44. A composition according to claim 42 wherein the humectant is glycerin.

45. A composition according to claim 41 which comprises about 1–12% by weight of said conditioning agent.

46. A composition according to claim 41 wherein the conditioning agent is an acrylamide polymer or copolymer.

47. A composition according to claim 41 wherein the conditioning agent is a hydroxyethylcellulose or guar gum.

48. A composition according to claim 41 which comprises about 0.1–3% of said surfactant.

49. A composition according to claim 41 wherein the surfactant comprises an amide diethanolamine.

50. A topically applied shaving composition for use by a human subject suffering from or prone to development of pseudofolliculitis barbae or razor bumps, said composition consisting of about 0.01–5% by weight of a bacteriostatic/hemostyptic agent selected from the group consisting of stannous fluoride, stannous bromide, sodium monofluorophosphate and combinations thereof, and said composition further consisting of an aqueous or water-miscible solvent, about 0.5–10% by weight of a cyclomethicone, a thickening agent and a cooling aid component.

51. A composition according to claim 50 wherein said cooling aid component comprises peppermint oil or menthol.

52. A topically applied shaving composition for use by a human subject suffering from or prone to development of pseudofolliculitis barbae or razor bumps, said composition consisting of about 0.01–5% by weight of a bacteriostatic/hemostyptic agent selected from the group consisting of stannous fluoride, stannous bromide, sodium monofluorophosphate and combinations thereof, and said composition further consisting of an aqueous or water-miscible solvent, about 0.5–10% by weight of a cyclomethicone, a thickening agent and a topical anesthetic agent selected from the group consisting of lidocaine or benzocaine.

* * * * *